(12) United States Patent
Hedberg et al.

(10) Patent No.: US 8,346,353 B2
(45) Date of Patent: Jan. 1, 2013

(54) IMPLANTABLE MEDICAL SYSTEM FOR DETECTING INCIPIENT EDEMA

(75) Inventors: Sven-Erik Hedberg, Kungsängen (SE); Andreas Blomqvist, Spånga (SE); Karin Järverud, Solna (SE); Karin Ljungström, Hässelby (SE); Leif Lindqvist, Stenhamra (SE); Urban Lönn, Uppsala (SE)

(73) Assignee: St. Jude Medical AB, Jarfalla (SE)

( * ) Notice: Subject to any disclaimer, the term of this patent is extended or adjusted under 35 U.S.C. 154(b) by 619 days.

(21) Appl. No.: 12/531,793

(22) PCT Filed: Apr. 24, 2007

(86) PCT No.: PCT/SE2007/000396
§ 371 (c)(1),
(2), (4) Date: Sep. 17, 2009

(87) PCT Pub. No.: WO2008/130291
PCT Pub. Date: Oct. 30, 2008

(65) Prior Publication Data
US 2010/0106210 A1 Apr. 29, 2010

(51) Int. Cl.
*A61B 5/05* (2006.01)
(52) U.S. Cl. ......... 600/547; 600/510; 600/538; 607/122
(58) Field of Classification Search ............... 607/122; 600/510, 547
See application file for complete search history.

(56) References Cited

U.S. PATENT DOCUMENTS

| | | | |
|---|---|---|---|
| 5,161,531 A | 11/1992 | Parsons et al. | |
| 6,332,091 B1 | 12/2001 | Burns et al. | |
| 6,409,675 B1 | 6/2002 | Turcott | |
| 7,010,337 B2 | 3/2006 | Furnary et al. | |
| 2002/0123674 A1 | 9/2002 | Plicchi et al. | |
| 2003/0199956 A1* | 10/2003 | Struble et al. | 607/122 |
| 2004/0102712 A1* | 5/2004 | Belalcazar et al. | 600/547 |
| 2005/0065559 A1* | 3/2005 | Bardy et al. | 607/5 |
| 2005/0148832 A1 | 7/2005 | Reghabi et al. | |
| 2005/0288759 A1* | 12/2005 | Jones et al. | 607/116 |
| 2006/0017575 A1 | 1/2006 | McAdams | |
| 2006/0074282 A1 | 4/2006 | Ward et al. | |

OTHER PUBLICATIONS

"Optical Measurement of Blood Oxygen by Implantable Telemetry," Schmitt, Stanford University Technical Report No. G558-15 (Feb. 1986).

* cited by examiner

*Primary Examiner* — Niketa Patel
*Assistant Examiner* — Hiba El-Kaissi (57) ABSTRACT

An implantable medical system for detecting incipient edema has an implantable medical lead including an optical sensor having a light source and a light detector. The medical system further has an edema detection circuit that activates the light source to emit light, the light being directed into lung tissue of a patient and that obtains a light intensity value corresponding to an intensity of light received by the light detector, and that evaluates the light intensity value to detect a consistency with incipient edema.

55 Claims, 6 Drawing Sheets

IMPLANTABLE MEDICAL SYSTEM FOR DETECTING INCIPIENT EDEMA

BACKGROUND OF THE INVENTION

1. Field of the Invention

The present invention generally relates implantable medical systems and, in particular, to systems, devices and methods for detecting incipient edema.

2. Description of the Prior Art

Pulmonary edema is often associated with heart failure.

In a healthy patient, the small alveoli in the lungs are filled with air. Close to the alveoli is a thin interstitial space, filled with interstitial fluid, which is different from blood. For example, the interstitial fluid contain no red blood cells. The interstitial space is also in close connection with capillaries filled with blood. Oxygen in the alveoli is diffusing into the interstitial space and then into the blood in the capillaries.

Development of pulmonary edema occurs gradually. For example, pulmonary edema may be a consequence of a heart failure. When the heart acquires a heart failure, the left arterial pressure and thereby the pressure in the capillaries will increase during a first phase. In this phase, no edema is present. In a second phase, the interstitial space between the alveoli and the capillaries is filled with more fluid, i.e., a swelling of the interstitial space occurs. The volume of the interstitial space increases with about two deciliters. In the following third, exacerbated phase, when the left arterial pressure has increased above 20, 25 mmHg, fluid enters the alveoli. Fluid in the alveoli diminishes the degree of oxygenation of the blood which weakens the heart and causes peripheral vasodilatation. The peripheral vasodilatation increases venous return from the peripheral circulation, which further increases the damming of blood in the alveoli, and thus, further diminishes the degree of oxygenation of the blood. This course of events may eventually lead to death of the patient. Pulmonary edema may develop so rapidly that death can occur within 20 minutes to an hour. Consequently, early detection of incipient edema is critical.

Pulmonary edema may be detected by using transthoracic impedance and through impedance measured between two implanted electrodes, covering one of the lungs. Edema has also been detected by listening to lung sounds.

Further, in U.S. Pat. No. 6,332,091, detection of pulmonary edema using infrared light is described. In a non-invasive method, a lung is exposed to infrared light and the reflected radiation scattered by the lung as a spectral response to the presence of water in the lung is measured. The reflected radiation is compared with calibrated values to evaluate an occurrence of pulmonary edema. The non-invasive method disclosed in U.S. Pat. No. 6,332,091 requires the use of external equipment, consequently pulmonary edema may only be detected in a patient at locations where such equipment is present.

In U.S. Pat. No. 7,010,337, a sensor for measuring transmission or reflection of light by the blood is described. The sensor is placed adjacent the aorta of a patient to evaluate the oxygen saturation of the blood passing in the aorta. Detection of edema is not discussed in U.S. Pat. No. 7,010,337.

In U.S. Pat. No. 6,409,675, a implantable monitor with one or more sensors configured for extravascular placement is described. The extravascular sensors include sensors for vascular plethysmography, heart and lung sounds, thoracic impedance, and EKG. For example, optical sensors adapted to determine arterial blood oxygen and arteriolar volume, and sound sensors adapted to detect pulmonary edema are disclosed. As alternate embodiments, detection of pulmonary edema utilizing thoracic impedance, ultrasound or analysis of Cheyne-Stokes respiration are disclosed.

Consequently, there remains a need within the art for an implantable medical system and a method using such system that are capable of detecting the occurrence of edema at an early stage, i.e. incipient edema.

SUMMARY OF THE INVENTION

Thus, an object of the present invention is to provide an implantable medical system, a lead and a method for detecting the occurrence of incipient edema.

Another object of the present invention is to provide an implantable medical system, a lead and a method for automatically detecting the occurrence of incipient edema.

A further object of the present invention is to provide an implantable medical system, a lead and a method for detecting incipient edema at an early stage.

These and other objects of the present invention are achieved by means of a medical system, a method and a computer-readable medium encoded with programming instructions According to an aspect of the present invention, a medical system for detecting incipient edema in a lung of a patient has an implantable medical lead including at least one optical sensor having at least one light source that emits light at least one predetermined wavelength and at least one predetermined intensity, and a light detector. The medical system further has an edema detection circuit that: i) activates the at least one light source to emit light, during at least one measurement session, at the at least one predetermined wavelength and at the at least one predetermined intensity, the light being directed into lung tissue of the patient; obtain at least one light intensity value corresponding to at least one intensity of light received by the light detector and resulting from the light emitted during a measurement session; and iii) evaluate the at least one light intensity value, including comparing the at least one light intensity value with at least one reference intensity value, to detect a consistency with incipient edema.

According to a second aspect of the present invention, there is provided an implantable medical lead including at least one optical sensor having at least one light source that emits light with at least one predetermined wavelength at least one predetermined intensity and a light detector. The implantable medical lead carries an edema detection circuit that: i) activates the at least one light source to emit light, during at least one measurement session, at the at least one predetermined wavelength and at the at least one predetermined intensity, the light being directed into lung tissue of the patient; obtains at least one light intensity value corresponding to at least one intensity of light received by the light detector and resulting from the light emitted during a measurement session; and ii) evaluates the at least one light intensity value, including comparing the at least one light intensity value with at least one reference intensity value, to detect a consistency with incipient edema.

According to a third aspect of the present invention, a method for detecting incipient edema in a lung of a patient uses a medical system having an implantable medical lead including at least one optical sensor carrying at least one light source adapted to emit light at least one predetermined wavelength at least one predetermined intensity and a light detector. The method includes the steps of: i) activating the at least one light source to emit light, during at least one measurement session, at the at least one predetermined wavelength and at the at least one predetermined intensity, the light being directed into lung tissue of the patient; ii) obtaining at least one light intensity value corresponding to at least one intensity of light received by the light detector and resulting from the light emitted during a measurement session; and iii) evaluating the at least one light intensity value, including comparing the at least one light intensity value with at least one reference intensity value, to detect a consistency with incipient edema.

According to a fourth aspect of the present invention, computer-readable medium is encoded with programming instructions and is directly loadable into an internal memory of an implantable device, the programming instructions causing the implantable medical device to perform steps in accordance with the method of the second aspect.

Edema is considered to be present at the stage when blood enters the alveoli. However, it is important to be able to detect developing edema at an earlier stage.

During the first phase of development of incipient edema, the capillaries close to the alveoli are congested and filled with more blood. The invention is based on the insight that physical changes of the lung of a patient, i.e. volume changes of fluids present in the lung, during the development of incipient edema will change intensities of light with certain wavelengths received by a light detector, wherein the light is emitted by a light source and the detected light has passed a part of the lung. In brief, there are three volume changes during the development of incipient edema that may, depending on the wavelength, change the intensity of the detected light: i) the blood congestion in capillaries during the first phase of development of incipient edema; ii) the swelling of the interstitial space during the second phase of development of incipient edema; and iii) the entry of fluids into the alveoli as the pulmonary edema eventually develops during the third, exacerbated phase. Wavelengths to be used in accordance with the invention comprise substantially all wavelengths which intensities are affected by these changes of volumes of fluids present in the lung.

In order to obtain reliable optical measurement of the change of the amount blood and other fluids in a lung, the light used for the measurement should pass into lung tissue, and not mainly being reflected against the surface of the lung. This may, for example, be accomplished by separating the light source and receiver apart. When the source and receiver are close, the majority of the light detected have been reflected against blood cells and similar tissues. In a report from Stanford University, Optical Measurement of blood oxygen by implantable telemetry, by Joseph Michael Schmitt, February 1986, Technical Report No. G558-15, a small light beam is entering a blood volume. Measurements of scattered intensity distributions show that main part of the amount of light is within one mm from the center of the beam. This part of the scattered light should not be allowed to reach the detector, which may be accomplished by letting the distance between source and detector be many times the distance used by Schmitt. The light entering the blood will be reflected against objects (such as blood cells) and be spread further away from the light source. The scattering will change the direction of the photons, which will spread in many directions. Therefore photons will penetrate deeper into lung tissue and eventually hit the receiver placed close to the surface of the lung. Along the path from source to detector not only scattering may occur, but also, for example, attenuation due to absorption. Both scattering and absorption may increase with increasing degree of edema, and consequently, the light intensity received by the detector may therefore mirror the amount of blood and fluid in the lung. As an example, consistency with incipient edema may be detected when the amount of light received is lower than a predetermined value.

Thus, the present invention provides a number of advantages, for example, an occurrence of an incipient edema in a patient can be detected at an early stage and the treatment of the incipient edema can thus be initiated at an early stage. This is of high importance since it has been shown that an early treatment is critical because an edema may develop very rapidly and cause death of the patient.

According to an embodiment, the edema detecting circuit, during the evaluation, obtains the at least one reference intensity value; and compare the at least one light intensity value with the at least one reference intensity value, wherein the consistency with incipient edema is detected when at least one of the at least one light intensity value is below the at least one reference intensity value. Consequently, it is possible to detect decreasing light intensity values being consistent with incipient edema.

According to an embodiment, the edema detection circuit, upon receiving a signal from a posture sensor, adapted to sense at least one predetermined posture of the patient, determines that the patient is in the at least one predetermined posture, and thereupon initiates the at least one measurement session. Consequently, it is possible to limit measurements to detect incipient edema to situations where the patient is in a suitable posture for making such measurements. Examples of suitable postures are lying on the back, lying on the side or lying on the stomach. Various reference values used during the measurement session may also be calculated as a function of the sensed posture. Measurements made with respect to the patients posture allows higher accuracy and reliability of the obtained values.

As an example, the edema detection circuit is adapted to determine the at least one reference intensity value as a function of the sensed at least one predetermined posture.

According to an embodiment, the edema detection circuit, upon obtaining the at least one light intensity value, activates a posture sensor adapted to sense at least one predetermined posture of the patient to determine a posture of the patient, and obtains the at least one reference intensity value being a function of the determined posture. Consequently, it is also possible to sense the posture and obtain a reference intensity value being a function the posture after obtaining a light intensity value.

In a further embodiment, the edema detection circuit determines the at least one reference intensity value as a function of a predetermined number of the obtained at least one light intensity values from previous measurement sessions. Consequently, a change in the light intensity values over time may be detected. Such change may be consistent with incipient edema.

According to an embodiment, the edema detection circuit compares at least one activity value obtained from an activity sensor adapted to sense at least one activity value corresponding to an activity level of the patient to a reference activity value and, when a predetermined number of the at least one activity values are below the reference activity value, and thereupon initiates the at least one measurement session. Consequently, it is possible to limit measurements to detect incipient edema to situations when the activity of the patient is sufficiently low. A high activity of the patient may render measurements to detect incipient edema in the patient uncertain, because the sensor of the implantable medical lead may move relative the lung of the patient. Measurements made with respect to the activity level of a patient allows higher accuracy and reliability of the obtained values.

According to an embodiment, the sensor is adapted to be arranged intrapericardially, epipericardially or in a coronary vein in the patient such that the light, upon activation of the at least one light source, is directed into a lung of the patient. Parts of the intrapericardial space, the epipericardial surface of the heart and the coronary veins are adjacent to the lung and consequently, detection of light which has passed a part of the lung is enabled by the above-mentioned arrangements.

According to an embodiment, the edema detection circuit activates alarm notifier adapted to communicate an alarm upon detection of incipient edema. As an example, the alarm notifier may generate a vibration or a beeping sound alerting the patient that a consistency with incipient edema has been detected. Consequently, the patient can be made aware of an incipient edema and seek medical assistance. Alternatively, or as a complement, the alarm notifier may include a telemetry circuit that sends information regarding the patients situation to an external device. Consequently, as an alternate or a complementary example, the alarm notification may sending a signal to an external device. For example, the external device may be connected via a communication network to a monitoring device, e.g. a PC, located at, for example, a care institution. Examples of communication networks are wireless LAN ("Local Area Network"), GSM ("Global System for Mobile communications"), UMTS ("Universal Mobile Telecommunications System") and the internet. Sending an alarm to an external device connected to a monitoring device may alert another person, such as a physician, of the patient's condition.

According to an embodiment, a lead length between the light source and the light detector is at least about 1 cm, preferably 1-10 cm, more preferably 1-7 cm, even more preferably 2-7 cm and most preferably 3-7 cm. Throughout the description and the claims, a lead length refers to a length along the lead. When the implantable medical lead is arranged in the body of a patient so as to direct light emitted by the light source into a lung of the patient, as a guiding appreciation not being limiting to the invention in any way, the greater the distance between the light source and the light detector, the greater the depth of the average path of the light which is detected by the light detector. In this context, depth refers to a distance from the implanted lead in a direction into the lung. Consequently, as an example, an appropriate lead length between the light source and the light detector may provide for that the light detected by the light detector has taken a sufficiently deep path through the lung of the patient to allow for a detection of an occurrence of incipient edema.

According to an embodiment, the implantable medical lead have rotation prevention structure that prevents rotation of the implantable medical lead relative the heart of the patient when implanted in the patient. Consequently, the movements of the implantable medical lead relative a lung of the patient may potentially be essentially limited to the movements of the heart relative the lung of a patient. Thus rotation prevention structure may allow for more accurate and reliable measurements.

As an example, the rotation prevention structure may be at least one protrusion extending from an envelope surface of the lead.

In one example, at least one rotation prevention means is arranged close to the light source and/or the light detector. Consequently, there is provided for a prevention of rotation of the part of the lead carrying the sensor.

According to an embodiment, the implantable medical lead has an orientation indicator that allows the rotational orientation of the implantable medical lead to be identified or detected during an implantation. The orientation revealing means may assist a physician during an implantation to orient the implantable medical lead such that light emitted from the light source, when the implantable medical lead is implanted, is directed into a lung of the patient. Further, the orientation indicator may assist a physician in verifying the position and orientation of the implantable medical lead after it has been implanted.

As an example, the orientation revealing indicator may be at least one marker that is detectable by X-ray. The at least one marker may be, for example, be L-shaped. Further, the marker may, for example, iridium and/or platinum. Iridium and platinum are advantageous materials because they are bio-compatible.

In one example, at least one orientation indicator is arranged close to the light source and/or the light detector. Such arrangement of the orientation revealing means allows for an appropriate orientation of the part of the lead carrying the sensor.

According to an embodiment, the edema detection circuit is in a implantable medical device connected to the implantable medical lead and that includes a pulse generator that generates cardiac stimulating pacing pulses. Consequently, it is possible to integrate the edema detection circuit in a pacemaker.

As an example, the implantable medical device further has a control circuit adapted to control pace pulse parameters, such as output voltage and pulse duration.

As an example, the implantable medical device further comprises a memory circuit, which may include a random access memory (RAM) and/or a non-volatile memory such as a read-only memory (ROM). The memory circuit may be adapted to store, for example, obtained light intensity values, predetermined reference values and/or generated reference values.

According to an embodiment, the at least one predetermined wavelength is in the range of 600-1400 nm, preferably 700-1000 nm, more preferably 760-860 nm and most preferably 800-820 nm. Penetration depth into human tissue is greatest for light with wavelengths in the red spectrum (625-760 nm) and the near infrared spectrum (750-1400 nm). As an example, a particularly preferable wavelength with regard to penetration of human tissue is 810 nm. Consequently, these wavelengths are examples of appropriate wavelengths for optical measurements of physical changes within the lung, such as volume changes of fluids present in the lung.

According to an embodiment, the at least one light source emits light with a first wavelength at a first intensity and a second wavelength at a second intensity and the edema detection circuit: i) activates the at least one light source to emit light, during at least one measurement session, at the first wavelength and the first intensity and at the second wavelength and the second intensity, the light being directed into lung tissue of the patient; ii) obtain at least one first intensity value corresponding to at least one intensity of light with the first wavelength and at least one second intensity value corresponding to at least one intensity of light with the second wavelength, with the intensities being received by the light detector and resulting from the light emitted during a measurement session; and iii) evaluate the at least one first intensity value and the at least one second intensity value, including comparing the at least one first intensity value and the at least one second intensity value with the at least one reference intensity value, to detect the consistency with incipient edema. By using two separate wavelengths during the measurements, it is possible reduce the number of false detections of occurrences of incipient edema caused by, for example, body movements.

As an example, the first wavelength is a wavelength being affected by changes of the volume of at least one predetermined fluid present in the lung, and the second wavelength is a wavelength not being substantially affected by changes of the volume of at least one predetermined fluid present in the lung. Consequently, by comparing the intensities of light of the first and the second wavelength, it may be verified that a change of the intensity of light of the first wavelength was caused by incipient edema and not, for example, body movements.

As an example, the edema detecting circuit, during the evaluation, obtains the at least one reference value, and at least one quotient of the at least one first intensity value and the at least one second intensity value with the at least one reference intensity value, with the consistency with incipient edema being detected when at least one of the at least one quotient is below the at least one reference intensity value.

DESCRIPTION OF THE PREFERRED EMBODIMENTS

In the following, the present invention will be discussed in the context of medical systems comprising at least an implantable device such as a pacemaker or an IDC and medical leads.

Figure 1:
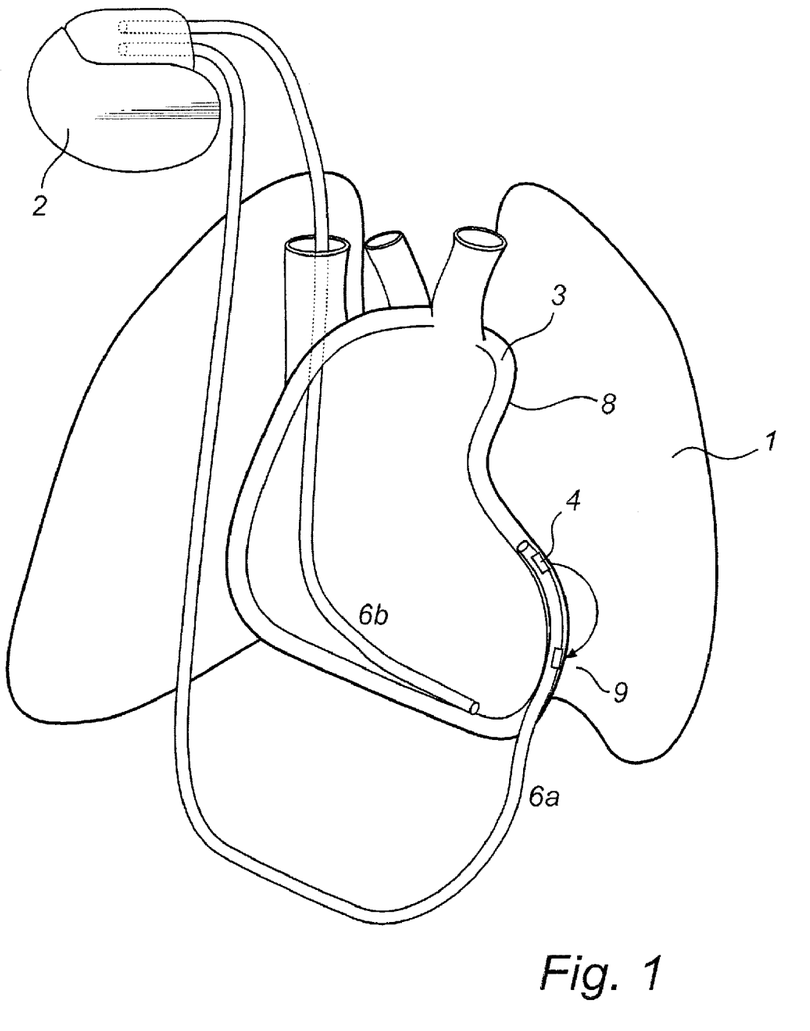
FIG. 1 schematically shows an embodiment of the invention in the context of a pacemaker system implanted in the body of a patient.

With reference to FIG. 1, there is shown a schematic diagram of a medical system according to one embodiment of the present invention. As seen, this embodiment of the present invention is shown in the context of a pacemaker 2 implanted in a patient (not shown). The pacemaker 2 has a housing that is hermetically sealed and biologically inert. Normally, the housing is conductive and may, thus, serve as an electrode. One or more pacemaker leads, where only two 6a, 6b are shown in FIG. 1, are electrically coupled to the pacemaker 2 in a conventional manner. The leads 6a, 6b extend into the heart 8. One or more conductive electrodes (not shown) for receiving electrical cardiac signals and/or for delivering electrical pacing to the heart 8 are arranged near the distal ends of the leads 6a, 6b. In this embodiment of the present invention, one lead 6a comprises a light source 4 and one light detector 9. The lead 6a is arranged in the intrapericardial space 3 of the heart 8 so as to direct light emitted from the light source 4 into a lung 1 of the patient. A certain amount of the light emitted by the light source 4, depending on, for example, the volumes of fluids present in the lung, is detected by the light detector 9. In alternate embodiments, the lead 6a may be arranged epipericardially or in a coronary vein. In principal, the lead 6a may be arranged in any way which allows light from the light source 4 to be directed into the lung 1 and detected by the light detector 9.

Figure 2:
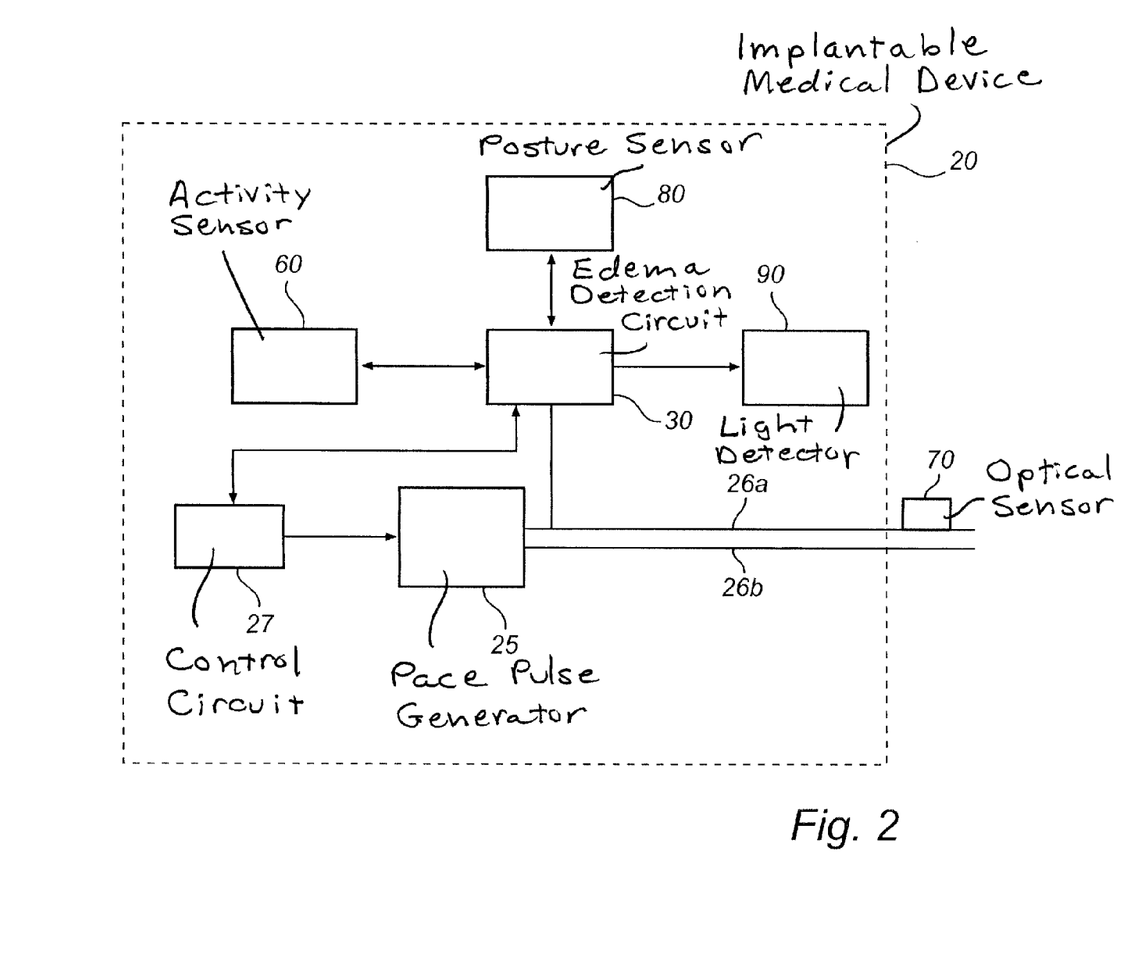
FIG. 2. schematically illustrates the configuration including the primary components of an embodiment of the present invention.

With reference now to FIG. 2, the configuration including the primary components of an embodiment of the present invention will be described. The illustrated embodiment comprises an implantable medical device 20, such as the pacemaker shown in FIG. 1, and leads 26a and 26b, of the same type as the leads 6a and 6b shown in FIG. 1, for delivering signals between the heart of the patient and the implantable medical device 20. The leads 26a, 26b may be electrically coupled to the pacemaker in a conventional manner. The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b carry one or more electrodes (as described with reference to FIG. 1), such as a tip electrode or a ring electrode, arranged to, inter alia, transmit pacing pulses for causing depolarization of cardiac tissue adjacent to the electrode(-s) generated by a pace pulse generator 25 under influence of a control circuit 27 including a microprocessor. The control circuit 27 controls, inter alia, pace pulse parameters such as output voltage and pulse duration. Further, an optical sensor 70, including a light source 4 that emits light at a predetermined wavelength and at a predetermined intensity and the light detector 9, which will be discussed in more detail with reference to FIG. 9, arranged in, for example, the lead 26a, that detects incipient edema in a lung 1 of a patient.

Furthermore, the optical sensor 70 is connected to an edema detection circuit 30. The edema detection circuit controls a measurement session. In the measurement session, the light source 4 is activated to emit light. When the lead 26a is properly implanted in the patient, the light from the light source is emitted into a lung of the patient, preferably the left lung. Part of the light emitted by the light source 4 reaches the light detector 9 after passing through a part of the lung, and, during the measurement session, a light intensity value corresponding to at least one intensity of light received by the light detector 9 is obtained. Subsequently, the at least one light intensity value obtained is evaluated to detect a consistency with incipient edema. The evaluation includes comparing the at least one light intensity value with at least one reference intensity value. As an example, a predetermined number of the at least one light intensity value being below the at least one reference intensity value may be considered to be consistent with incipient edema. Each value may be calculated as an average value over a predetermined number of values or of values obtained over a predetermined period of time or as a weighted average value over a predetermined number of values or of values obtained over a predetermined period of time.

The edema detection circuit 30 may be connected to an activity sensor 60 that senses at least one activity value corresponding to an activity level of the patient. For example, the activity sensor may be an accelerometer. The accelerometer may be a piezoelectric sensor of a conventional type. The edema detection circuit may, for example, be adapted to compare the at least one activity value to a reference activity value and, when a predetermined number of the at least one activity value is below the reference activity value and/or when light intensity values obtained over a predetermined period of time are below the reference activity value, initiate the measurement session. Each light intensity value may be calculated as an average light intensity value over a predetermined number of light intensity values or of light intensity values obtained over a predetermined period of time or as a weighted average light intensity value over a predetermined number of light intensity values or of light intensity values obtained over a predetermined period of time.

The edema detection circuit 30 may be also connected to a posture sensor 80 that senses at least one predetermined posture (P) of the patient. As an example, the edema detection circuit may initiate such posture sensing and, upon receiving a signal from the posture sensor that the patient is in the at least one predetermined posture, initiate the measurement session described above. As an alternate example, the edema detection circuit is adapted to, upon obtaining the at least one light intensity value, initiate posture sensing and obtain the reference intensity value being a function of the determined posture.

Further, the edema detection circuit 30 may be connected to an alarm notifier 90 that generates an alarm when a consistency of incipient edema is detected by the edema detection circuit. The alarm notifier may cause the device to vibrate or to deliver a beeping sound in order to alert the patient of the situation. Alternatively, or as a complement, the alarm notifier 90 may send information regarding the patients situation to an external device via a telemetry circuit. For example, the external device may be connected via a communication network to a monitoring device, e.g. a PC, located at, for example, a care institution. Examples of communication networks are wireless LAN ("Local Area Network"), GSM ("Global System for Mobile communications"), UMTS ("Universal Mobile Telecommunications System") and the internet. For a given communication method, a multitude of standard and/or proprietary communication protocols may be used. For example, and without limitation, wireless (e.g. radio frequency pulse coding, spread spectrum frequency hopping, time-hopping, etc.) and other communication protocols (e.g. SMTP, FTP, TCP/IP) may be used. Other proprietary methods and protocols may also be used. The monitoring device may assist a physician in diagnosing the patient and deciding the appropriate actions, for example whether the patient should be called in to a clinic.

The patient status may be determined by means of a reference value set including at least one reference intensity values. Predefined reference values can be stored in and obtained from an internal memory circuit (not shown), which may include a random access memory (RAM) and/or a non-volatile memory such as a read-only memory (ROM). As an example, the internal memory circuit may be an integral part of the control circuit 27 or the edema detection circuit 30. Alternatively, the predefined reference values may be obtained from an external device via a telemetry circuit. As an alternate example, the reference values may be created by the implantable medical device by performing at least one reference measurement session during conditions found to be stable, for example, with respect to physiological parameters such as body temperature, heart rate, posture, activity and minute ventilation, and stored in the internal memory circuit. The created reference values may be stored in, and obtained from, the above-mentioned internal memory circuit. The reference value set may constitute an indication of an initial patient status for use when determining a development of incipient edema or a trend of a certain parameter. In addition to reference intensity values, examples of reference values comprise reference activity values. Each reference value may be calculated as an average reference value over a predetermined number of reference values or of reference values obtained over a predetermined period of time or as a weighted average reference value over a predetermined number of reference values or of reference values obtained over a predetermined period of time.

Further, the edema detection circuit 30 may be adapted to calculate the reference intensity values and/or the reference activity values as a function of the posture (P) sensed by the posture sensor.

Figure 3:
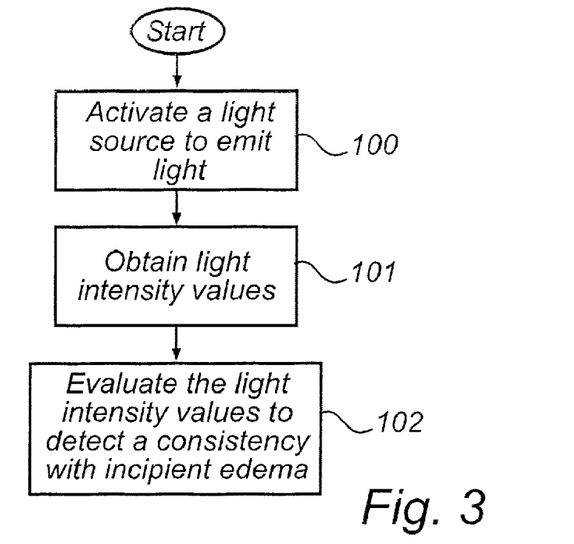
FIG. 3. is a high level flow chart in accordance with an embodiment of the present invention.

Turning now to FIG. 3, a high-level description of an embodiment of the invention for detecting incipient edema in a lung of a patient, using a medical system comprising an implantable medical lead including at least one optical sensor comprising at least one light source adapted to emit light with at least one predetermined wavelength at least one predetermined intensity and a light detector, is shown. At step 100, the light source is activated to emit light at the predetermined wavelength at the at least one predetermined intensity. The light is emitted into the lung of the patient. In one embodiment, the light source is activated at periodic intervals. In another embodiment, the light source is activated when at least one physical parameter, such as the activity and/or posture of the patient, is appropriate. As an example, the at least one physical parameter is measured at periodic intervals and, when the at least one physical parameter is found to be appropriate, the light source is activated.

At step 101, at least one light intensity value corresponding to at least one intensity of light received by the light detector and resulting from the light emitted from the light source is obtained, wherein the light has passed a part of the lung. As an example, the optical sensor is arranged at the left side of the heart in such manner that the light received by the light detector has passed a part of the lung being close to the left side of the heart, such as a part of the lung being within a distance of 3 cm of the intrapericardial space of the heart. As an example, the at least one light intensity value may correspond to at least one average of intensities of light received over a predetermined number of intensities of light received or of intensities of light received over a predetermined period of time or as a weighted average intensity of light received over a predetermined number of intensities of light received or of intensities of light received over a predetermined period of time. Further, each light intensity value may be calculated as an average light intensity value over a predetermined number of light intensity values or of light intensity values obtained over a predetermined period of time or as a weighted average light intensity value over a predetermined number of light intensity values or of light intensity values obtained over a predetermined period of time.

At step 102, the at least one light intensity value obtained in step 101 is evaluated to detect a consistency with incipient edema. The evaluation may include comparing the at least one light intensity value with at least one reference intensity value. The reference intensity value may be obtained from a memory circuit. As an example, the reference intensity value may be a predetermined value. As an alternate example, the reference intensity value may be a function of at least one previously obtained light intensity value as described above in the discussion about reference values. In another embodiment, the reference intensity value is obtained from an external device outside the human body via a telemetry circuit adapted to receive reference intensity values. The reference intensity values received from the external device may be set with respect to a physicians diagnosis of the patient or information in a patient register in a database. Further, any reference intensity value obtained, independent of its origin, may be calculated with respect to physiological parameters such as body temperature, heart rate, activity level, patient posture and/or minute ventilation. The invention is based on the insight that the light intensity values changes when incipient edema develops because volumes of fluids present in the lung changes. Consequently, a consistency with incipient edema may be detected when a comparison of the at least one light intensity value with the at least one reference value reveals a change. The type and magnitude of change which is considered to be consistent with incipient edema may vary with the wavelength of the light because intensities of light with different wavelengths are affected differently by the changes of volumes of different fluids present in the lung. For example, a change which is considered to be consistent with incipient edema may correspond to a limit reference intensity value, wherein one or more light intensity values below such limit reference intensity value are considered to be consistent with incipient edema. Each of the one or more light intensity values may be calculated as an average light intensity value over a predetermined number of light intensity values or of light intensity values obtained over a predetermined period of time or as a weighted average light intensity value over a predetermined number of light intensity values or of light intensity values obtained over a predetermined period of time.

Figure 4:
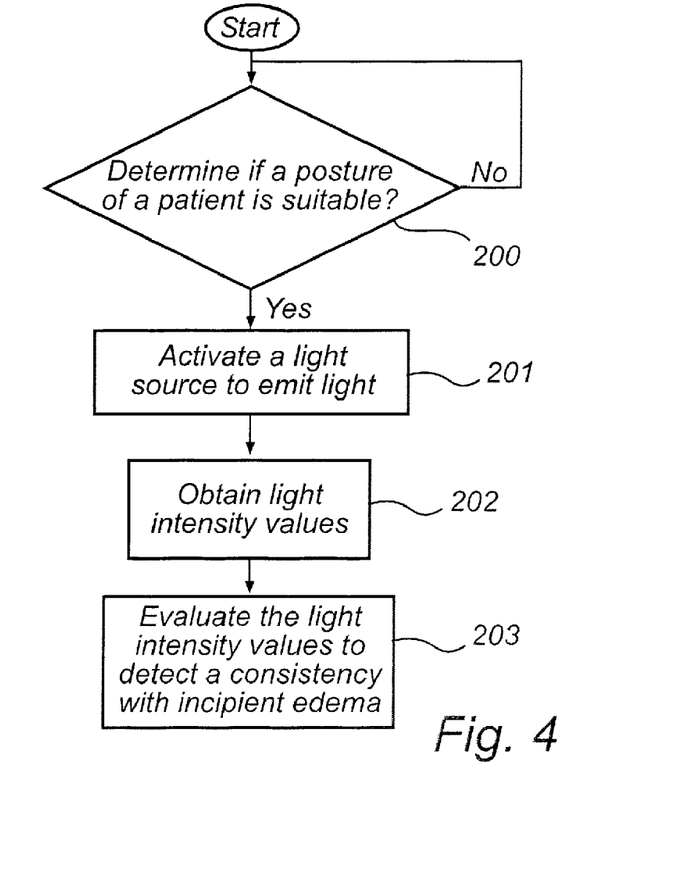
FIG. 4. is another high level flow chart in accordance with an embodiment of the present invention.

Referring now to FIG. 4, a high-level description of another embodiment of the invention is shown. At step 200, a posture of the patient is determined using a posture sensor adapted to sense at least one predetermined posture of the patient. If the sensed posture is suitable, a measurement session comprising steps 201, 202, and 203 corresponding to steps 100, 101, and 102 described above, respectively, is initiated. For example, a suitable posture of the patient may be a horizontal position, such as lying on the back, lying on the side or lying on the stomach. If the posture sensing indicates that the patient is not in a suitable position, step 200 is repeated, for example, after a predetermined time or after a time being a function of the sensed posture.

Figure 5:
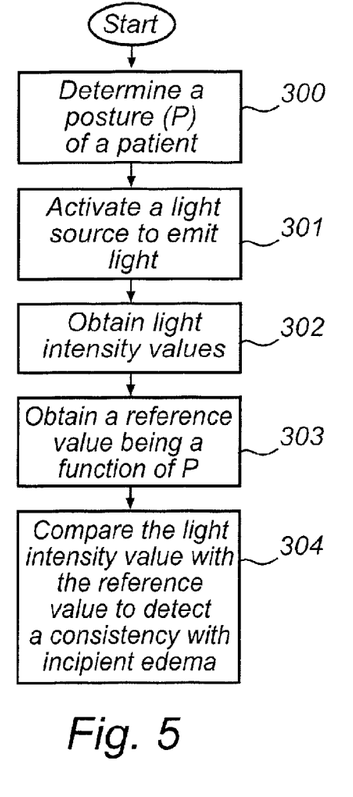
FIG. 5. is another high level flow chart in accordance with an embodiment of the present invention.

Referring now to FIG. 5, a high level description of another embodiment of the invention is shown. At step 300, a posture (P) of the patient is determined by a posture sensor adapted to sense at least one predetermined posture of the patient. The subsequent steps 301 and 302 corresponds to steps 100 and 101 described above, respectively. At step 303, at least one reference intensity value being a function of the posture (P) determined at step 300 is obtained. Each reference intensity value being a function of P may, for example, be calculated as an average reference intensity value over a predetermined number of reference intensity values obtained when the patient was in P or of values obtained when the patient was in P over a predetermined period of time or as a weighted reference intensity average value over a predetermined number of reference intensity values obtained when the patient was in P or of reference intensity values obtained when the patient was in P over a predetermined period of time. Alternatively, or as a complement, the reference intensity value may be weighted with respect to P according to a predetermined algorithm. At step 304, the at least one light intensity value obtained in step 302 is compared with the at least one reference intensity value obtained in 303 to detect a consistency with incipient edema. As described above with reference to step 102, a consistency with incipient edema may be detected when a comparison of the at least one light intensity value with the at least one reference value reveals a change. In one embodiment, the consistency with incipient edema is detected when at least one of the at least one light intensity values is below the at least one reference intensity value.

Figure 6:
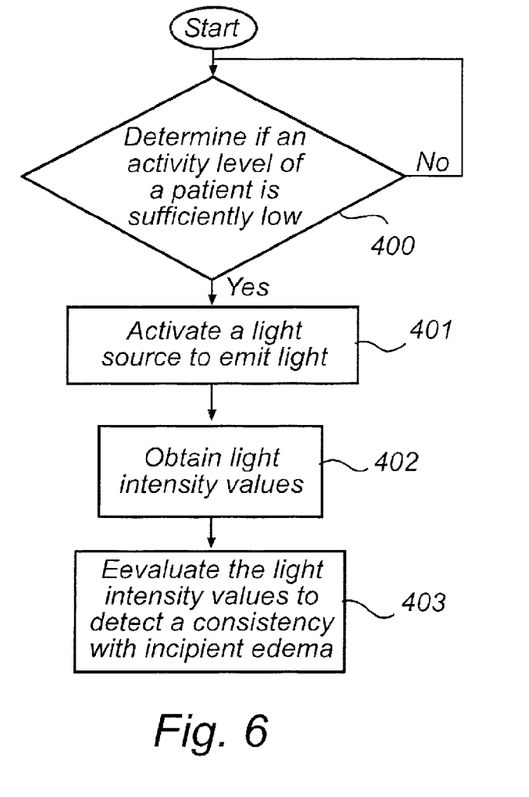
FIG. 6. is another high level flow chart in accordance with an embodiment of the present invention.

Referring now to FIG. 6, a high level description of another embodiment of the invention is shown. At step 400, an activity of the patient is determined using a activity sensor adapted to sense at least one activity value corresponding to an activity level of the patient. If the at least one activity value is sufficiently low, a measurement session comprising steps 401, 402 and 403 corresponding to steps 100, 101, and 102 described above, respectively, is initiated. To determine if the at least one activity value is sufficiently low, the at least one activity value may be compared with a reference intensity value. As an example, the measurement session may be initiated if a predetermined number of the at least one activity values are below the reference activity value. The reference activity value may be obtained from a memory circuit. As an example, the reference activity value may be a predetermined value. As an alternate example, the reference activity value may be a function of at least one previously obtained light activity value as described above in the discussion about reference values. If the determined activity is found not to be sufficiently low, step 400 is repeated, for example, after a predetermined time or after a time being a function of a sensed posture. As an example, if posture sensing has indicated that the patient is in a horizontal position, such as lying on the back, lying on the side or lying on the stomach, step 400 may be repeated with a shorter interval than if posture sensing has indicated that the patient is in an standing position.

Figure 7:
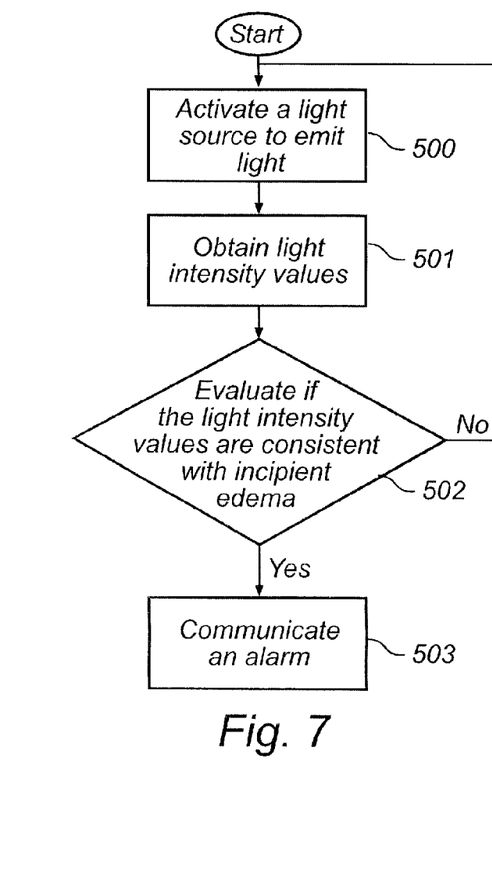
FIG. 7. is another high level flow chart in accordance with an embodiment of the present invention.

Referring now to FIG. 7, a high level description of another embodiment of the invention is shown. Steps 500 and 501 corresponds to the steps 100 and 101 described above, respectively. At step 502, the at least one light intensity value obtained in step 501 is evaluated to detect a consistency with incipient edema. The evaluation in 502 corresponds to the evaluation in step 102 described above. If a consistency with incipient edema is not detected at step 502, a measurement session comprising the steps 500, 501 and 502 are repeated, for example, after a predetermined time or after a time being a function of the at least one light intensity value obtained in step 501. As an example, if the evaluation in step 502 reveals that the obtained at least one light intensity value is close to values being considered to be consistent with incipient edema, the measurement session may be repeated with a shorter interval than if the obtained at least one light intensity value were far from values being considered to be consistent with incipient edema. If a consistency with incipient edema is detected at step 502, alarm means adapted to communicate an alarm is activated at step 503. As an example, the alarm may be a vibration or a beeping sound alerting the patient that incipient edema is present. Alternatively, or as a complement, the alarm may comprise sending information regarding the patients situation to an external device via a telemetry circuit. The external device may be connected via a communication network to a monitoring device as described above.

Figure 8:
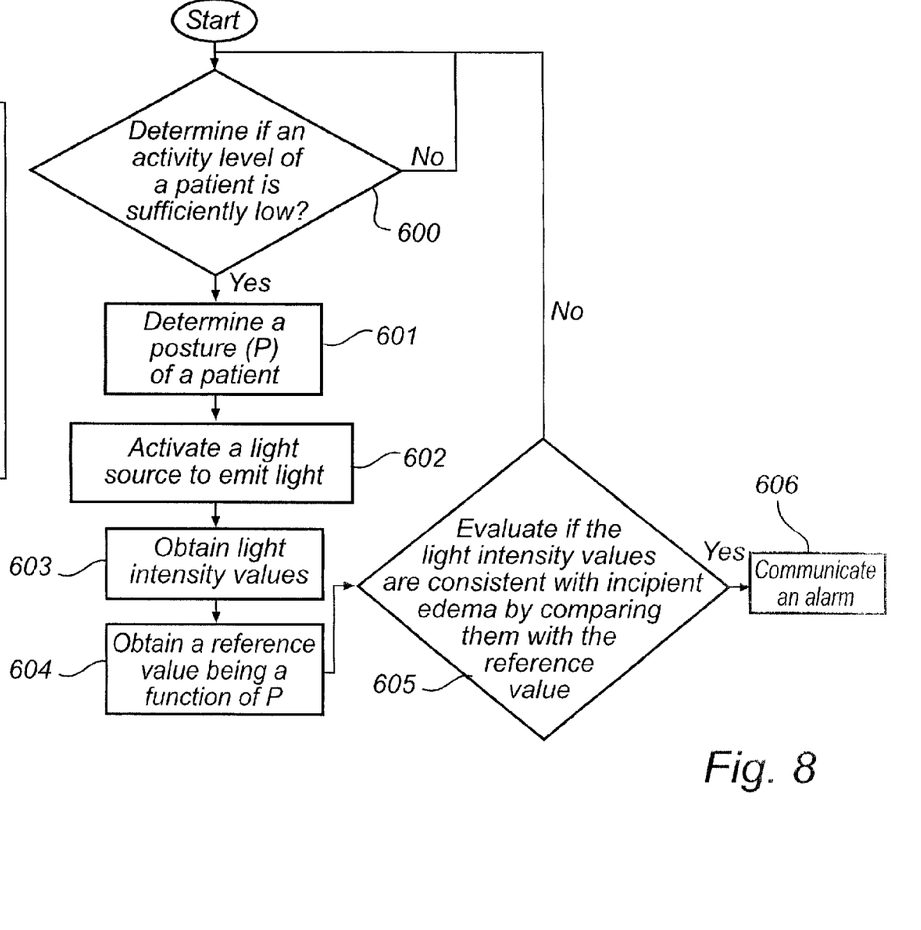
FIG. 8. is another high level flow chart in accordance with an embodiment of the present invention.

Referring now to FIG. 8, a high level description of another embodiment of the invention is shown. At step 600, an activity of the patient is determined. Step 600 corresponds to step 400 described above. If the determined activity is sufficiently low, a posture (P) of the patient is determined at step 601. Step 601 corresponds to step 300 described above. The subsequent steps of activating a light source to emit light 602, obtaining at least one light intensity value 603 and obtaining at least one reference value being a function of P 604 corresponds to the steps 301, 302 and 303 described above, respectively. At step 605, the at least one light intensity values obtained in step 603 is compared to the at least one reference light intensity value obtained in step 604 to detect a consistency with incipient edema. The comparison of step 605 corresponds to that of step 304 described above. If a consistency with incipient edema is not detected in step 605, a measurements session comprising the steps 600-605 is repeated, for example after a predetermined time or after a time being a function of one or more physical parameters, such as the posture (P) determined in step 601 or the at least one light intensity value obtained in step 604. As an example, if posture sensing has indicated that the patient is in a horizontal position, such as lying on the back, lying on the side or lying on the stomach, the measurement session may be repeated with a shorter interval than if posture sensing has indicated that the patient is in an standing position. Alternatively, or as a complement, if the comparison in step 605 reveals that the obtained at least one light intensity value were close to values being considered to be consistent with incipient edema, the measurement session may be repeated with a shorter interval than if the obtained at least one light intensity value were far from values being considered to be consistent with incipient edema. If a consistency with incipient edema is detected at step 605, alarm means adapted to communicate an alarm is activated at step 606. The step 606 corresponds to step 503 described above.

Figure 9:
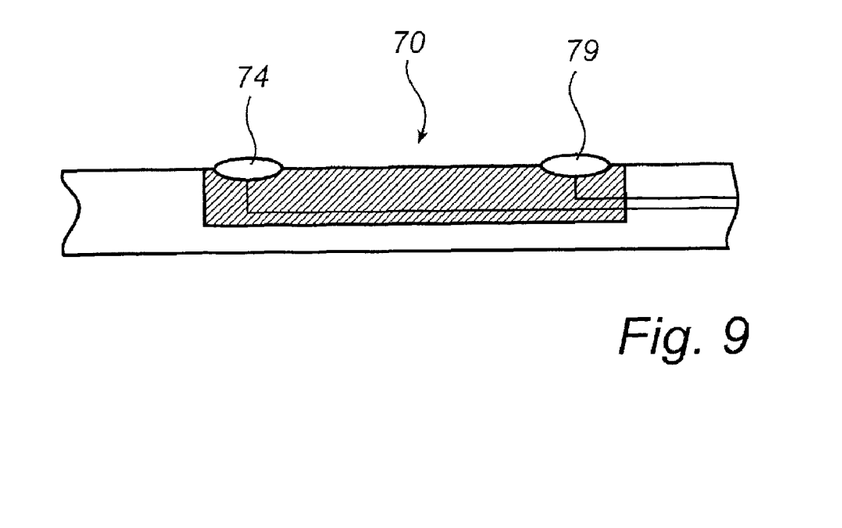
FIG. 9 schematically illustrates a cross-sectional view of an embodiment of the sensor according to the present invention.

Turning now to FIG. 9, a cross-sectional view of an optical sensor 70 for use in accordance with the invention is shown. This example embodiment of the sensor 70 is arranged in a implantable medical lead. The optical sensor has a light source 74 that emits light with at least one predetermined wavelength at least one predetermined intensity. As an example, the light source 74 may be an light-emitting diode. For example, the light-emitting diode may be emitting light in the range of 600-1400 nm, preferably 700-1000 nm, more preferably 760-860 nm and most preferably 800-820 nm. For example, the light source may be an infrared diode emitting light of about 810 nm. The optical sensor further has a light detector 79 that detects light emitted by the light source 74. As an example, the light detector may be a photodiode. The light source 74 and the light detector 79, respectively, are electrically connected to an edema detection circuit (not shown), which connections are adapted to transmit signals from the edema detection signals to the light source and from the light detector to the edema detection circuit. The edema detection circuit may be arranged in the implantable medical lead or, alternatively, in a implantable medical device connected to the implantable medical lead.

Figure 10:
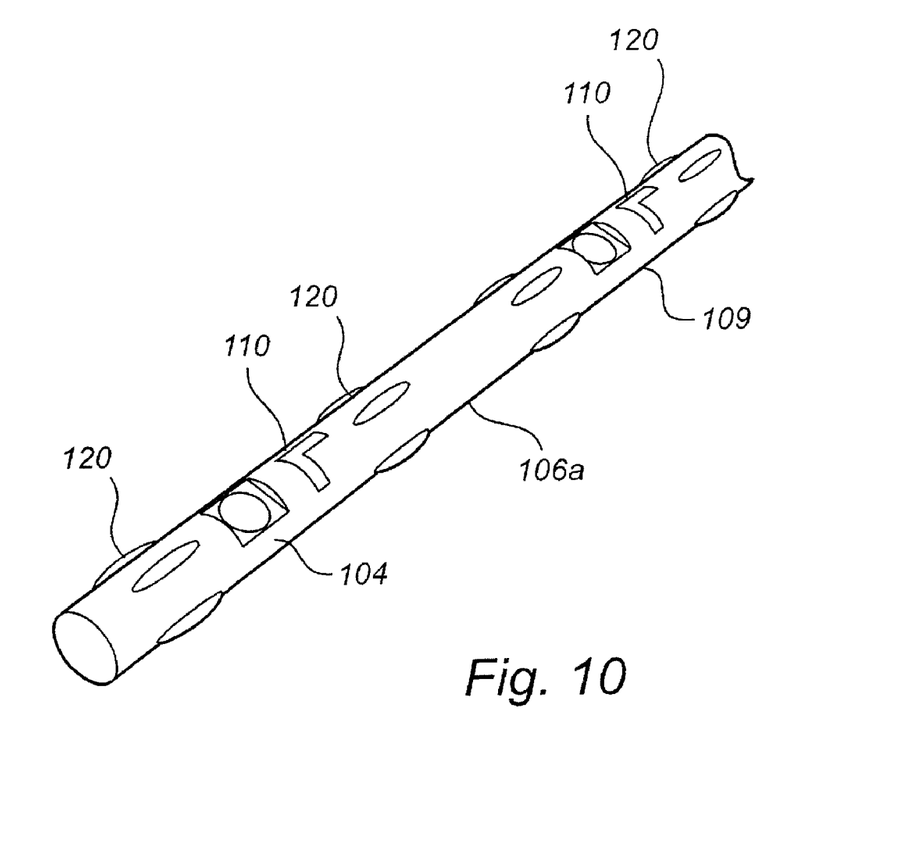
FIG. 10 schematically illustrates an embodiment of an implantable medical lead according to the present invention.

Referring now to FIG. 10, a implantable medical lead 106a for use in accordance with the invention is shown. The implantable medical lead has an optical sensor comprising a light source 104 and a light detector 109 corresponding to the light source 74 and light detector 79 described above, respectively. When the implantable medical lead is arranged in the body of a patient so as to direct light emitted by the light source into a lung of the patient, as a guiding appreciation not being limiting to the invention in any way, the greater the distance between the light source 74 and the light detector 79, the greater the depth of the average path of the light which is detected by the detector. In this context, depth refers to a distance from the implanted lead in a direction into the lung. Thus, the lead length between the light source 74 and the light detector 79 may be any lead length providing for a sufficient depth for detecting incipient edema according to the invention. As an example, a lead length between the light source and the light detector is at least about 1 cm, preferably 1-7 cm, more preferably 2-7 cm, most preferably 3-7 cm. A cross-section of the implantable lead 106a may have any appropriate geometrical shape. As an example, for intrapericardial arrangement, the shape of the cross-section of the implantable medical lead 106a may be essentially flat or essentially oval. As another example, for arrangement in a coronary vein, the shape of the cross-section of the implantable medical lead 106a may be essentially circular.

The implantable medical lead 106a further has a orientation indicating structure 110 that allows an rotational orientation of the implantable medical lead during 106a an implantation to be detected. The orientation indicating structure 110 may assist a physician during an implantation to orient the implantable medical lead 106a such that light emitted from the light source 104 is directed into a lung of the patient when the implantable medical lead 106a is implanted. As an example, the orientation indicating structure 110 is at least one marker being detectable by X-ray. The at least one marker may, for example, be L-shaped. Further, the at least one marker may, for example, be iridium and/or platinum. As an example, orientation indicating structure 110 is arranged close to the light source 104 and/or the light detector 109, such as within a lead length of 5 cm of the light source 104 and/or light detector 109, such as within a lead length of 4 cm of the light source 104 and/or light detector 109, such as within a lead length of 3 cm of the light source 104 and/or light detector 109, such as within a lead length of 2 cm of the light source 104 and/or light detector 109, such as within a lead length of 1 cm of the light source 104 and/or light detector 109.

The implantable medical lead 106a has rotation prevention structure 120 that prevents rotation of the implantable medical lead 106a relative a heart of the patient when implanted in the patient. As an example, the rotation prevention structure 120 may comprise at least one protrusion extending from an envelope surface of the implantable medical lead 106a. For example, at least one pair of protrusions may extend from the implantable medical lead 106a in opposite directions such that the pair form a plane. As an example, at least one rotation prevention means 120 is arranged close to the light source 104 and/or the light detector 109, such as within a lead length of 5 cm of the light source 104 and/or light detector 109, such as within a lead length of 4 cm of the light source 104 and/or light detector 109, such as within a lead length of 3 cm of the light source 104 and/or light detector 109, such as within a lead length of 2 cm of the light source 104 and/or light detector 109, such as within a lead length of 1 cm of the light source 104 and/or light detector 109.

Although modifications and changes may be suggested by those skilled in the art, it is the intention of the inventors to embody within the patent warranted heron all changes and modifications as reasonably and properly come within the scope of their contribution to the art.

We claim as our invention:

1. A medical system comprising: an implantable medical lead adapted for implantation in a patient, said implantable medical lead carrying at least one optical sensor comprising a light source configured to emit light in vivo at a predetermined wavelength and at a predetermined intensity, said optical sensor further comprising a light detector, said implantable medical lead being configured to direct the light emitted by said light source into lung tissue of the patient; and an edema detection circuit connected to said implantable medical lead, said edema detection circuit being configured to activate said light source to emit light during at least one measurement session at said predetermined wavelength and said predetermined intensity and, with said light detector, to detect said light after said light interacts with said lung tissue, the light detected by the light detector having a detected light intensity value, and to evaluate said detected light intensity value by comparing said detected light intensity value with a reference intensity value to obtain a comparison result, and to emit an edema detection circuit output indicating incipient edema when said comparison result is consistent with incipient edema.

2. A medical system as claimed in claim 1 wherein said edema detecting circuit is configured to determine that said comparison result is consistent with incipient edema when said detected light intensity value is below said reference intensity value.

3. A medical system as claimed in claim 1 comprising a posture sensor configured to detect a predetermined posture of the patient, and wherein said edema detection circuit is configured to, upon receiving a signal from said posture sensor that said patient is in said predetermined posture, initiates said measurement session.

4. A medical system as claimed in claim 3 wherein said edema detection circuit is configured to obtain said reference intensity value as a function of said predetermined posture.

5. A medical system as claimed in claim 1 comprising a posture sensor configured to detect a predetermined posture of the patient, and wherein said edema detection circuit is configured to, upon obtaining said detected light intensity value, initiate a posture sensing with said posture sensor to determine a posture of the patient, and wherein said edema detection circuit obtains said reference intensity value as a function of the posture detected by said posture sensor.

6. A medical system as claimed in claim 1 wherein said edema detection circuit is configured to determine said reference intensity value as a function of a predetermined number of detected light intensity values respectively from a plurality of previous measurement sessions.

7. A medical system as claimed in claim 1 comprising an activity sensor configured to sense at least one activity value representing a physical activity level of the patient, and wherein said edema detection circuit is configured to repeatedly compare said activity value to a reference activity value and, when a predetermined number of activity values are below said reference activity value, initiate said measurement session.

8. A medical system as claimed in claim 1 wherein said medical lead is configured for implantation at a location selected from the group consisting of an intrapericardial location, an epipericardial location, and in a coronary vein of the patient.

9. A medical system as claimed in claim 1 comprising an alarm notifier configured to emit a humanly perceptible alarm when said edema detection circuit emits said output indicating incipient edema.

10. A medical system as claimed in claim 1 wherein said implantable medical lead carries said light source and said light detector with a lead length therebetween that is selected from the group consisting of about 1 cm, in a range between 1 and 7 cm, in a range between 2 and 7 cm, and in a range between 3 and 7 cm.

11. A medical system as claimed in claim 1 wherein said implantable medical lead comprises rotation preventing structure configured to prevent in vivo rotation of the implantable medical lead relative to the heart of the patient.

12. A medical system as claimed in claim 11 wherein said rotation preventing structure comprises at least one protrusion extending from an exterior surface of the implantable medical lead.

13. A medical system as claimed in claim 1 wherein said implantable medical lead comprises an orientation indicator configured to indicate a rotational orientation of said implantable medical lead during implantation of said implantable medical lead.

14. A medical system as claimed in claim 13 wherein said orientation indicator comprises at least one x-ray-detector marker.

15. A medical system as claimed in claim 1 wherein said edema detection circuit is integrated with said optical sensor.

16. A medical system as claimed in claim 1 comprising: a housing configured for implantation in the patient; a pulse generator in said housing configured to emit cardiac stimulating pulses; and said edema detection circuit also being contained in said housing, and being connected to said pulse generator for modifying generation of said cardiac stimulating pulses dependent on said output indicating incipient edema.

17. A medical system as claimed in claim 1 wherein said predetermined wavelength is in a range selected from the group consisting of 600-1400 nm, 700-1000 nm, 760-860 nm, and 800-820 nm.

18. A medical system as claimed in claim 1 wherein said predetermined wavelength is a first wavelength and said predetermined intensity is a first intensity, and wherein: said light source emits light at said first wavelength at said first intensity and at a second wavelength at a second intensity, said light at said second wavelength at said second intensity also being directed in vivo at lung tissue; said edema detection circuit is configured to activate said light source to emit light, during said measurement session, at said first wavelength at said first intensity, and at said second wavelength at said second intensity; said light detector being configured to detect said light at said first wavelength at said first intensity to obtain a detected first intensity value, and to detect said light at said second wavelength at said second intensity to detect a second detected intensity value; and said edema detection circuit being configured to evaluate said first detected intensity value and said second detected intensity value by comparing said first detected intensity value and said second detected intensity value with said reference intensity value to generate said comparison result.

19. A medical system as claimed in claim 18 wherein said edema detection circuit is configured to compare a quotient of said first detected intensity value and said second detected intensity value with said reference intensity value, and to determine consistency of said comparison result with incipient edema when said quotient is below said reference intensity value.

20. An implantable medical lead comprising: an implantable lead body adapted for implantation in a patient, said implantable lead body carrying at least one optical sensor comprising a light source configured to emit light in vivo at a predetermined wavelength and at a predetermined intensity, and a light detector, said implantable lead body being configured to direct the light emitted by said light source into lung tissue of the patient; and an edema detection circuit carried by said implantable lead body, said edema detection circuit being configured to activate said light source to emit light during at least one measurement session at said predetermined wavelength and said predetermined intensity and, with said light detector, to detect said light after said light interacts with said lung tissue, the light detected by the light detector having a detected light intensity value, and to evaluate said detected light intensity value by comparing said detected light intensity value with a reference intensity value to obtain a comparison result, and to emit an edema detection circuit output indicating incipient edema when said comparison result is consistent with incipient edema.

21. An implantable medical lead as claimed in claim 20 wherein said edema detecting circuit is configured to determine that said comparison result is consistent with incipient edema when said detected light intensity value is below said reference intensity value.

22. An implantable medical lead as claimed in claim 20 comprising a posture sensor configured to detect a predetermined posture of the patient, and wherein said edema detection circuit is configured to, upon receiving a signal from said posture sensor that said patient is in said predetermined posture, initiates said measurement session.

23. An implantable medical lead as claimed in claim 22 wherein said edema detection circuit is configured to obtain said reference intensity value as a function of said predetermined posture.

24. An implantable medical lead as claimed in claim 20 comprising a posture sensor configured to detect a predetermined posture of the patient, and wherein said edema detection circuit is configured to, upon obtaining said detected light intensity value, initiate a posture sensing with said posture sensor to determine a posture of the patient, and wherein said edema detection circuit obtains said reference intensity value as a function of the posture detected by said posture sensor.

25. An implantable medical lead as claimed in claim 20 wherein said edema detection circuit is configured to determine said reference intensity value as a function of a predetermined number of detected light intensity values respectively from a plurality of previous measurement sessions.

26. An implantable medical lead as claimed in claim 20 comprising an activity sensor configured to sense at least one activity value representing a physical activity level of the patient, and wherein said edema detection circuit is configured to repeatedly compare said activity value to a reference activity value and, when a predetermined number of activity values are below said reference activity value, initiate said measurement session.

27. An implantable medical lead as claimed in claim 20 wherein said implantable lead body is configured for implantation at a location selected from the group consisting of an intrapericardial location, an epipericardial location, and in a coronary vein of the patient.

28. An implantable medical lead as claimed in claim 20 comprising an alarm notifier configured to emit a humanly perceptible alarm when said edema detection circuit emits said output indicating incipient edema.

29. An implantable medical lead as claimed in claim 20 wherein said implantable lead body carries said light source and said light detector with a lead length therebetween that is selected from the group consisting of about 1 cm, in a range between 1 and 7 cm, in a range between 2 and 7 cm, and in a range between 3 and 7 cm.

30. An implantable medical lead as claimed in claim 20 wherein said implantable lead body comprises rotation preventing structure configured to prevent in vivo rotation of the implantable lead body relative to the heart of the patient.

31. An implantable medical lead as claimed in claim 30 wherein said rotation preventing structure comprises at least one protrusion extending from an exterior surface of the implantable lead body.

32. An implantable medical lead as claimed in claim 20 wherein said implantable lead body comprises an orientation indicator configured to indicate a rotational orientation of said implantable lead body during implantation of said implantable medical lead.

33. An implantable medical lead as claimed in claim 32 wherein said orientation indicator comprises at least one x-ray-detector marker.

34. An implantable medical lead as claimed in claim 20 wherein said edema detection circuit is integrated with said optical sensor.

35. An implantable medical lead as claimed in claim 20 wherein said predetermined wavelength is in a range selected from the group consisting of 600-1400 nm, 700-1000 nm, 760-860 nm, and 800-820 nm.

36. An implantable medical lead as claimed in claim 20 wherein said predetermined wavelength is a first wavelength and said predetermined intensity is a first intensity, and wherein: said light source emits light at said first wavelength at said first intensity and at a second wavelength at a second intensity, said light at said second wavelength at said second intensity also being directed in vivo at lung tissue; said edema detection circuit is configured to activate said light source to emit light, during said measurement session, at said first wavelength at said first intensity, and at said second wavelength at said second intensity; said light detector being configured to detect said light at said first wavelength at said first intensity to obtain a detected first intensity value, and to detect said light at said second wavelength at said second intensity to detect a second detected intensity value; and said edema detection circuit being configured to evaluate said first detected intensity value and said second detected intensity value by comparing said first detected intensity value and said second detected intensity value with said reference intensity value to generate said comparison result.

37. An implantable medical lead as claimed in claim 36 wherein said edema detection circuit is configured to compare a quotient of said first detected intensity value and said second detected intensity value with said reference intensity value, and to determine consistency of said comparison result with incipient edema when said quotient is below said reference intensity value.

38. A method for detecting incipient edema comprising the steps of: Implanting a medical lead in a patient, and with said implantable medical lead, carrying at least one optical sensor comprising a light source that emits light in vivo at a predetermined wavelength and at a predetermined intensity, and a light detector, said medical lead, when implanted, causing the light emitted by said light source to be directed into lung tissue of the patient; and with an edema detection circuit connected to said implantable medical lead, activating said light source to emit light during at least one measurement session at said predetermined wavelength and said predetermined intensity and, with said light detector, detecting said light after said light interacts with said lung tissue, the light detected by the light detector having a detected light intensity value, and automatically evaluating said detected light intensity value by comparing said detected light intensity value with a reference intensity value to obtain a comparison result, and emitting an edema detection circuit output indicating incipient edema when said comparison result is consistent with incipient edema.

39. A method as claimed in claim 38 comprising, with said edema detecting circuit, determining that said comparison result is consistent with incipient edema when said detected light intensity value is below said reference intensity value.

40. A method as claimed in claim 38 comprising detecting a predetermined posture of the patient, and with said edema detection circuit, upon receiving a signal from said posture sensor that said patient is in said predetermined posture, initiating said measurement session.

41. A method as claimed in claim 40 comprising, with said edema detection circuit, obtaining said reference intensity value as a function of said predetermined posture.

42. A method as claimed in claim 38 comprising detecting a predetermined posture of the patient, and with said edema detection circuit, upon obtaining said detected light intensity value, initiating a posture sensing to determine a posture of the patient, and with said edema detection circuit, obtaining said reference intensity value as a function of the detected posture.

43. A method as claimed in claim 38 comprising, with said edema detection circuit, determining said reference intensity value as a function of a predetermined number of detected light intensity values respectively from a plurality of previous measurement sessions.

44. A method as claimed in claim 38 comprising sensing at least one activity value representing a physical activity level of the patient, and with said edema detection circuit, repeatedly comparing said activity value to a reference activity value and, when a predetermined number of activity values are below said reference activity value, initiating said measurement session.

45. A method as claimed in claim 38 comprising implanting said medical lead at a location selected from the group consisting of an intrapericardial location, an epipericardial location, and in a coronary vein of the patient.

46. A method as claimed in claim 38 comprising emitting a humanly perceptible alarm when said edema detection circuit emits said output indicating incipient edema.

47. A method as claimed in claim 38 comprising, on said implantable medical lead, carrying said light source and said light detector with a lead length therebetween that is selected from the group consisting of about 1 cm, in a range between 1 and 7 cm, in a range between 2 and 7 cm, and in a range between 3 and 7 cm.

48. A method as claimed in claim 38 comprising providing said implantable medical lead with rotation preventing structure that prevents in vivo rotation of the implantable medical lead relative to the heart of the patient.

49. A method as claimed in claim 48 comprising forming said rotation preventing structure as at least one protrusion extending from an exterior surface of the implantable medical lead.

50. A method as claimed in claim 38 comprising providing said implantable medical lead with an orientation indicator that indicates a rotational orientation of said implantable medical lead during implantation of said implantable medical lead.

51. A method as claimed in claim 50 comprising forming said orientation indicator as at least one x-ray-detector marker.

52. A method as claimed in claim 38 comprising: from a pulse generator, emitting cardiac stimulating pulses; and with said edema detection circuit, modifying generation of said cardiac stimulating pulses dependent on said output indicating incipient edema.

53. A method as claimed in claim 38 emitting said light at said predetermined wavelength in a range selected from the group consisting of 600-1400 nm, 700-1000 nm, 760-860 nm, and 800-820 nm.

54. A method as claimed in claim 38 wherein said predetermined wavelength is a first wavelength and said predetermined intensity is a first intensity, and comprising: emitting light from said light source at said first wavelength at said first intensity and at a second wavelength at a second intensity, said light at said second wavelength at said second intensity also being directed in vivo at lung tissue; with said edema detection circuit, activating said light source to emit light, during said measurement session, at said first wavelength at said first intensity, and at said second wavelength at said second intensity; with said light detector, detecting said light at said first wavelength at said first intensity to obtain a detected first intensity value, and detecting said light at said second wavelength at said second intensity to detect a second detected intensity value; and in said edema detection circuit, evaluating said first detected intensity value and said second detected intensity value by comparing said first detected intensity value and said second detected intensity value with said reference intensity value to generate said comparison result.

55. A method as claimed in claim 54 comprising, said edema detection circuit, comparing a quotient of said first detected intensity value and said second detected intensity value with said reference intensity value, and determining consistency of said comparison result with incipient edema when said quotient is below said reference intensity value.

* * * * *